US012447263B2

(12) United States Patent
Levy et al.

(10) Patent No.: US 12,447,263 B2
(45) Date of Patent: Oct. 21, 2025

(54) APPARATUS AND METHOD FOR PRODUCING AN ENRICHED MEDICAL CONTRAST SUSPENSION

(71) Applicants: Frank Levy, Fort Myers, FL (US); Kimberley Levy, Fort Myers, FL (US)

(72) Inventors: Frank Levy, Fort Myers, FL (US); Kimberley Levy, Fort Myers, FL (US)

( * ) Notice: Subject to any disclaimer, the term of this patent is extended or adjusted under 35 U.S.C. 154(b) by 1801 days.

(21) Appl. No.: 16/376,291

(22) Filed: Apr. 5, 2019

(65) Prior Publication Data

US 2019/0307948 A1 Oct. 10, 2019

Related U.S. Application Data

(60) Provisional application No. 62/653,648, filed on Apr. 6, 2018.

(51) Int. Cl.

| | |
|---|---|
| ***A61M 5/00*** | (2006.01) |
| ***A61M 5/20*** | (2006.01) |
| ***A61M 5/31*** | (2006.01) |
| ***A61M 11/00*** | (2006.01) |
| ***A61M 25/00*** | (2006.01) |

(52) U.S. Cl.

CPC .......... *A61M 5/007* (2013.01); *A61M 5/2053* (2013.01); *A61M 5/31* (2013.01); *A61M 11/007* (2014.02); *A61M 25/0026* (2013.01); *A61M 2005/3128* (2013.01); *A61M 2202/0225* (2013.01); *A61M 2202/0468* (2013.01); *A61M 2206/20* (2013.01)

(58) Field of Classification Search

CPC .. A61M 5/007; A61M 11/007; A61M 5/2053; A61M 5/31; A61M 25/0026; A61M 2005/3128; A61M 2202/0225; A61M 2202/0468; A61M 2206/20; A61M 11/06; A61M 2025/0073; A61M 35/00; A61M 25/0071; A61M 3/005; A61M 16/12–16/125; A61M 5/2066; A61M 5/3294; A61M 16/127; A61M 2005/006; A61B 8/481; A61J 1/2089

See application file for complete search history.

(56) References Cited

U.S. PATENT DOCUMENTS

| | | |
|---|---|---|
| 2,475,511 A | 7/1949 | Nicholson |
| 2,828,889 A | 4/1958 | Joschko |
| 3,831,844 A | 8/1974 | Tropeano et al. |
| 5,154,248 A | 10/1992 | Ratnik et al. |
| 5,246,140 A | 9/1993 | Thix et al. |

(Continued)

FOREIGN PATENT DOCUMENTS

| | | |
|---|---|---|
| EP | 2548607 A2 | 1/2013 |
| JP | 2013536020 A | 9/2013 |

(Continued)

*Primary Examiner* — James D Ponton
*Assistant Examiner* — Hong-Van N Trinh
(74) *Attorney, Agent, or Firm* — Welsh Flaxman & Gitler LLC

(57) ABSTRACT

A medical contrast suspension generating delivery apparatus includes a Venturi-agitating tip assembly, a source of pressurized medical carbon dioxide, a source of an iodinated contrast medium, and a dual lumen catheter connecting the Venturi-agitating tip assembly to the source of pressurized medical carbon dioxide and the source of the iodinated contrast medium.

10 Claims, 9 Drawing Sheets

(56) References Cited

U.S. PATENT DOCUMENTS

| | | | | |
|---|---|---|---|---|
| 5,345,932 | A | 9/1994 | Yafuso et al. | |
| 5,395,318 | A | 3/1995 | Kaprelian | |
| 5,580,530 | A | 12/1996 | Kowatsch et al. | |
| 5,699,961 | A | 12/1997 | Ratnik et al. | |
| 5,875,776 | A | 3/1999 | Vaghefi | |
| 5,964,223 | A * | 10/1999 | Baran | A61M 16/0486 128/207.14 |
| 6,164,559 | A | 12/2000 | Dupre et al. | |
| 6,402,047 | B1 | 6/2002 | Thomas | |
| 6,474,091 | B2 | 11/2002 | Guerra | |
| 6,572,873 | B1 | 6/2003 | Osman et al. | |
| 7,543,760 | B2 | 6/2009 | Levy et al. | |
| 8,876,749 | B2 | 11/2014 | Levy | |
| 9,744,342 | B2 | 8/2017 | Levy | |
| 10,155,093 | B2 | 12/2018 | Levy et al. | |
| 10,322,271 | B2 | 6/2019 | Levy et al. | |
| 10,350,398 | B2 | 7/2019 | Levy et al. | |
| 10,350,399 | B2 | 7/2019 | Levy et al. | |
| 2001/0004461 | A1 | 6/2001 | Moore, Jr. et al. | |
| 2001/0044618 | A1 | 11/2001 | Recinella et al. | |
| 2001/0056233 | A1 | 12/2001 | Uber, III et al. | |
| 2002/0055682 | A1 | 5/2002 | Griffiths et al. | |
| 2006/0007109 | A1 | 1/2006 | Noritake | |
| 2006/0007438 | A1 | 1/2006 | Chen | |
| 2006/0017862 | A1 | 1/2006 | Song et al. | |
| 2006/0071091 | A1 | 4/2006 | Ratnik | |
| 2006/0074386 | A1 | 4/2006 | Wollmann | |
| 2006/0178620 | A1 | 8/2006 | Wollmann et al. | |
| 2007/0104651 | A1 | 5/2007 | Wright et al. | |
| 2007/0244429 | A1 | 10/2007 | Nguyen et al. | |
| 2008/0012099 | A1 | 1/2008 | Yeh et al. | |
| 2008/0016762 | A1 | 1/2008 | Emalfarb | |
| 2008/0120992 | A1 | 5/2008 | Levy et al. | |
| 2008/0167621 | A1 | 7/2008 | Wagner et al. | |
| 2009/0006274 | A1 | 1/2009 | Levin et al. | |
| 2009/0031889 | A1 | 2/2009 | Saul et al. | |
| 2009/0062741 | A1 | 3/2009 | Smith et al. | |
| 2009/0318890 | A1 | 12/2009 | Levy | |
| 2010/0015288 | A1 | 1/2010 | Fukuda et al. | |
| 2010/0152880 | A1 | 6/2010 | Boyden et al. | |
| 2011/0021841 | A1 | 1/2011 | Chen et al. | |
| 2011/0218411 | A1 | 9/2011 | Keenan et al. | |
| 2012/0030566 | A1 | 2/2012 | Victor | |
| 2012/0305669 | A1 | 12/2012 | Meron et al. | |
| 2016/0166782 | A1 * | 6/2016 | Levy | A61K 9/0019 604/507 |
| 2016/0213835 | A1 * | 7/2016 | Levy | A61M 5/1452 |
| 2017/0361077 | A1 | 12/2017 | Levy et al. | |
| 2019/0070397 | A1 | 3/2019 | Levy et al. | |

FOREIGN PATENT DOCUMENTS

| | | | |
|---|---|---|---|
| WO | 9300951 | A1 | 1/1993 |
| WO | 2000/072821 | A1 | 12/2000 |
| WO | 2002/041872 | A1 | 5/2002 |
| WO | 02/43795 | A1 | 6/2002 |
| WO | 2005/048984 | A1 | 6/2005 |

* cited by examiner

APPARATUS AND METHOD FOR PRODUCING AN ENRICHED MEDICAL CONTRAST SUSPENSION

CROSS REFERENCE TO RELATED APPLICATION

This application claims the benefit of U.S. Provisional Patent Application Ser. No. 62/653,648, entitled "APPARATUS AND METHOD FOR PRODUCING AN ENRICHED MEDICAL CONTRAST SUSPENSION," filed Apr. 6, 2018.

BACKGROUND OF THE INVENTION

1. Field of the Invention

This invention relates to an apparatus and process for producing an enriched medical contrast suspension composed of an iodinated contrast medium and $CO_2$.

2. Description of the Related Art

The present invention utilizes the Venturi effect to produce an enriched medical contrast solution. The Venturi effect is an example of Bernoulli's principle, in the case of incompressible fluid, flow through a tube or pipe with a constriction in it. The fluid velocity must increase through the constriction to satisfy the equation of continuity, while its pressure must decrease due to conservation of energy; the gain in kinetic energy is supplied by a drop in pressure or a pressure gradient force.

The limiting case of the Venturi effect is choked flow, in which a constriction in a pipe or channel limits the total flow rate through the channel because the pressure cannot drop below zero in the constriction. Choked flow is used to control the delivery rate of water and other fluids through spigots and other types of valves. The portable apparatus of the present invention utilizes a source of pressurized medical fluid, to produce the desired pressure and flow for the effective creation of an enriched medical contrast solution.

SUMMARY OF THE INVENTION

It is, therefore, an object of the present invention to provide a medical contrast suspension generating delivery apparatus including a Venturi-agitating tip assembly, a source of pressurized medical carbon dioxide, a source of an iodinated contrast medium, and a dual lumen catheter connecting the Venturi-agitating tip assembly to the source of pressurized medical carbon dioxide and the source of the iodinated contrast medium.

It is also an object of the present invention to provide a medical contrast suspension generating delivery apparatus wherein the source of pressurized medical carbon dioxide includes a pressure delivery syringe of a compressed medical fluid unit.

It is another object of the present invention to provide a medical contrast suspension generating delivery apparatus wherein the source of the iodinated contrast medium includes a contrast syringe.

It is a further object of the present invention to provide a medical contrast suspension generating delivery apparatus wherein a micro-hose connects the source of pressurized medical carbon dioxide to a first lumen of the dual lumen catheter.

It is also an object of the present invention to provide a medical contrast suspension generating delivery apparatus wherein the source of the iodinated contrast medium is connected to the second lumen of the dual lumen catheter to deliver the iodinated contrast medium to the second lumen of the dual lumen catheter.

It is another object of the present invention to provide a medical contrast suspension generating delivery apparatus wherein the contrast syringe includes a one-way valve at its outlet to ensure that iodinated contrast medium from the contrast syringe only flows out of the contrast syringe.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to the various figures and embodiments, the medical contrast suspension generating delivery apparatus 1 includes a Venturi-agitating tip assembly (various embodiments of which are described below) composed of a multi-channel arrangement at a proximal first end thereof and a tip at a distal second end thereof. The delivery apparatus 1 also includes a compressed medical fluid unit 12 supplying pressurized medical carbon dioxide ($CO_2$) 13 fluidly connected to the multi-channel arrangement at the proximal first end of the Venturi-agitating tip assembly and a medical iodinated contrast medium 15 fluidly connected to the multi-channel arrangement at the proximal first end of the Venturi-agitating tip assembly. Pressurized medical carbon dioxide ($CO_2$) 13, from the compressed medical fluid unit 12, and the iodinated contrast medium 15 are combined within the Venturi-agitating tip assembly in a manner generating a medical contrast suspension that is ultimately dispensed from the delivery catheter. A method in accordance with the apparatus is also disclosed.

Figure 1:
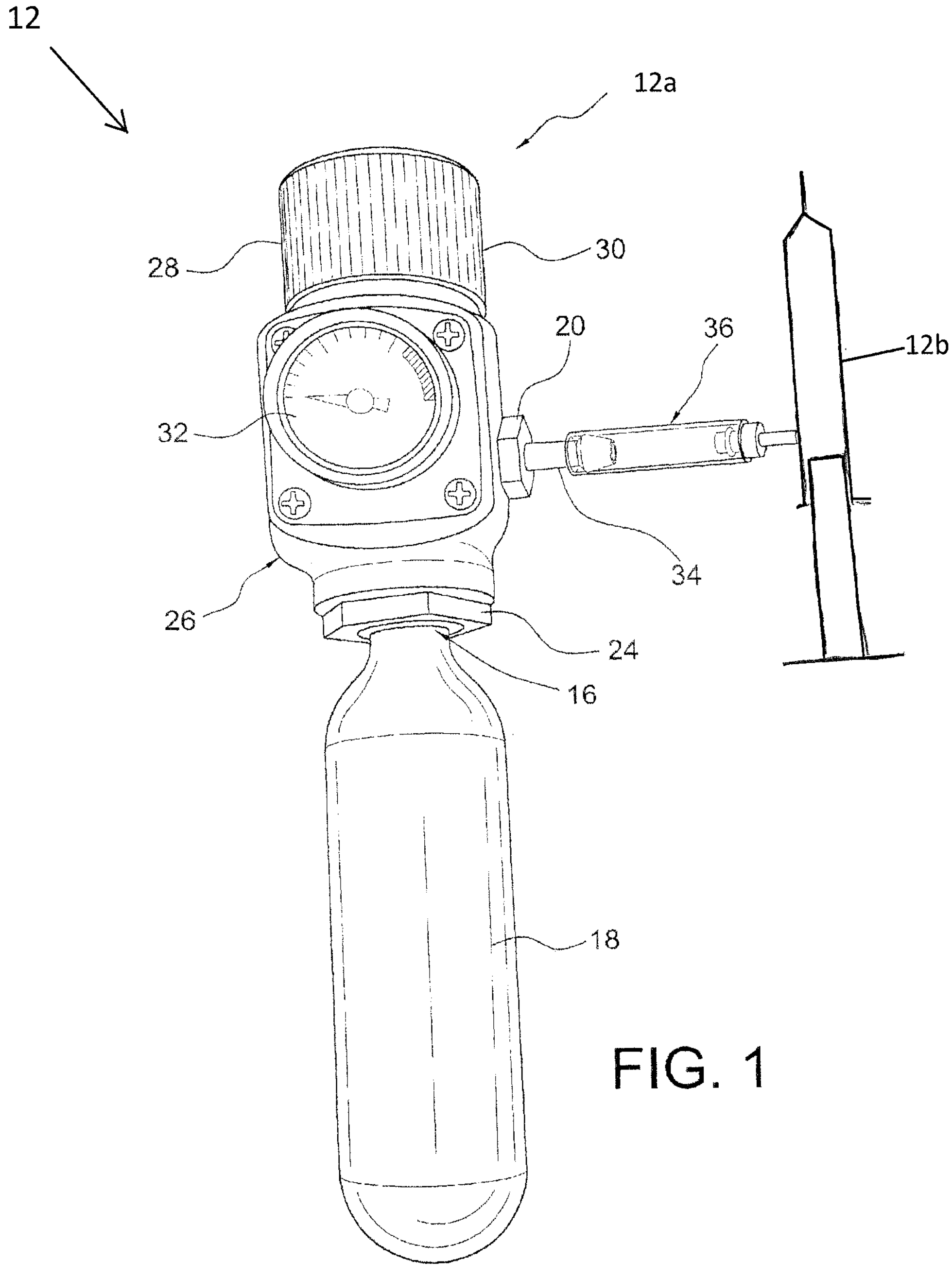
FIG. 1 is a perspective view of the compressed medical fluid unit including a supply unit with a capsule secured thereto and a pressure delivery syringe.
Figure 3:
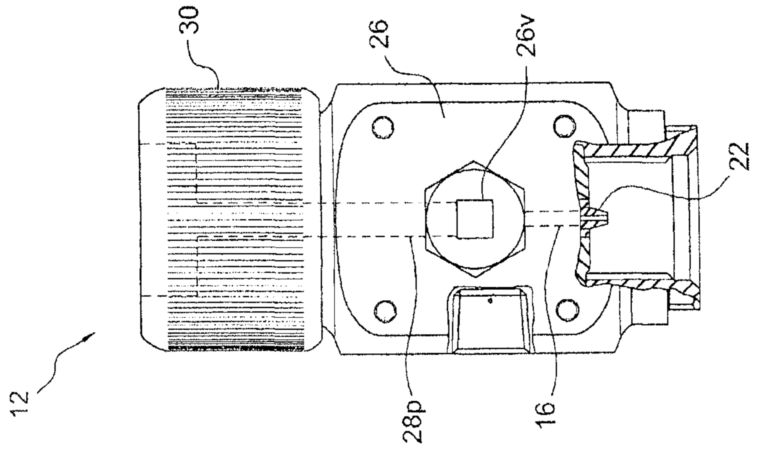
FIG. 3 is a side elevation view of the supply unit shown in FIG. 2 with a partial cutaway of the fitting to show the cylinder cartridge puncture valve.
Figure 2:
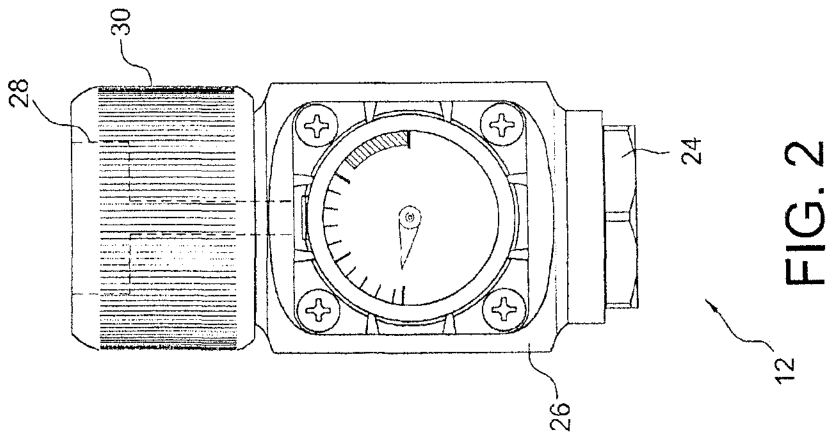
FIG. 2 is a front elevation view of the supply unit.

With reference to FIGS. 1, 2 and 3, the compressed medical fluid unit 12 is disclosed. The compressed medical fluid unit 12 includes a supply unit 12*a* as disclosed in detail in U.S. Pat. No. 9,427,522, filed Sep. 26, 2014 and issued Aug. 30, 2016, entitled "DELIVERY SYSTEM FOR THE EFFECTIVE, RELIABLE AND FOOLPROOF DELIVERY OF CONTROLLED AMOUNTS OF A MEDICAL FLUID," which is incorporated herein by reference, and a pressure delivery syringe 12*b*. The supply unit 12*a* delivers high pressure gas, in particular medical carbon dioxide ($CO_2$) to the pressure delivery syringe 12*b*, which then forces the pressurized carbon dioxide ($CO_2$) 13 into a delivery catheter 2. With reference to FIGS. 1, 2 and 3, the supply unit 12*a* includes an inlet port 16 to which a source of pressurized medical carbon dioxide ($CO_2$), for example, a pressurized gas cylinder containing medical carbon dioxide ($CO_2$) 18 is selectively connected, and an outlet port 20 in communication with the inlet port 16, and ultimately the at least one pressurized gas ($CO_2$) cylinder 18.

The pressurized gas cylinder 18 is secured to, and maintained in fluid communication with, the integrated supply unit 12*a* by a cylinder cartridge puncture valve 22 and a fitting 24 formed at the inlet port 16 of the supply unit 12*a*. In accordance with a preferred embodiment, the cylinder cartridge puncture valve 22 has a mechanism for piercing the pressurized gas cylinder 18, as is known in the art, and for holding or securing the pressurized gas cylinder 18 in place.

The pressurized gas, that is, pressurized medical carbon dioxide ($CO_2$), exits the inlet port 16 and passes through a regulator valve assembly 26 controlled by a press button actuator 28 and regulator adjustment dial 30. The regulator valve assembly 26 dictates the pressure of the gas as it ultimately exits the outlet port 20. In accordance with a preferred embodiment, the regulator valve assembly 26 has a selective outlet pressure in the range of 7 psi to 19 psi. The desired outlet pressure is achieved by rotating the regulator adjustment dial 30 of the button actuator 28 until the desired pressure is achieved as identified via the PSI pressure gauge 32. In addition to regulating the applied pressure, the regulator valve assembly 26 also includes a valve 26*v* that controls the passage of gas from the inlet port 16 to the outlet port 20. The valve 26*v* is controlled via a push button mechanism 28*p* in the button actuator 28 such that a user may selectively determine when gas may pass therethrough to the outlet port 20. In accordance with a preferred embodiment, the $CO_2$ flow rate is less than 12 NL/min (normal liters per minute).

As mentioned above, the regulator valve assembly 26 also includes a regulator adjustment dial 30 which controls the pressure of the medical carbon dioxide ($CO_2$) permitted to exit the outlet port 20 by either rotating the regulator adjustment dial 30 clockwise or counterclockwise as may be desired to adjust the applied pressure. The applied pressure is monitored using the PSI pressure gauge 32 formed on the front face of the supply unit 12*a*.

In practice, a pressurized gas cylinder 18 is applied to the supply unit 12*a* in the following manner. The adjustment dial 30 is first rotated to its off position, at which point the supply unit 12*a* is in its fully closed orientation. The pressurized gas cylinder 18 is then screwed into the fitting 24 and the cylinder cartridge puncture valve 22 punctures pressurized gas cylinder 18. The adjustment dial 30 is then turned clockwise to open the supply unit 12*a* and allow for flow therethrough. The supply unit 12*a* is then actuated by twisting the adjustment dial further in a clockwise direction until a desired pressure is established. The supply unit 12*a* is then operated as described above, through the manipulation of the press button actuator 28 and the adjustment dial 30.

As mentioned above, the outlet port 20 is in fluid communication with the inlet port 16 for transport of pressurized medical carbon dioxide ($CO_2$) in accordance with the present invention. The outlet port 20 is provided with a luer connection 34 for the secure and selective attachment of an outlet tube 36 thereto. The outlet tube 36 is secured to the main body of the pressure delivery syringe 12*b* for the supply of pressurized medical carbon dioxide ($CO_2$) 13 to the pressure delivery syringe 12*b* in accordance with the present invention. Once the pressure delivery syringe 12*b* is filled with pressurized medical carbon dioxide ($CO_2$) 13, the pressure delivery syringe 12*b* may then be used to force the pressurized medical carbon dioxide ($CO_2$) 13 through the delivery catheter as described below.

As briefly mentioned above, the pressurized gas cylinder 18 is secured to the supply unit 12*a* by a cartridge puncture valve 22 as is commonly known. Pressurized medical carbon dioxide ($CO_2$) 13 leaves the regulator valve assembly 26 at the regulator adjusted pressure and goes to the outlet port 20.

In accordance with an alternative embodiment, an integrated compressed medical fluid unit as disclosed in U.S. Pat. No. 9,662,435, filed Sep. 26, 2014 and issued May 30, 2017, entitled "SYSTEM AND METHOD FOR THE EFFECTIVE, RELIABLE AND FOOLPROOF DELIVERY OF CONTROLLED AMOUNTS OF A MEDICAL FLUID," which is incorporated herein by reference, may be utilized in accordance with the present invention instead of the supply unit described above.

Figure 4:
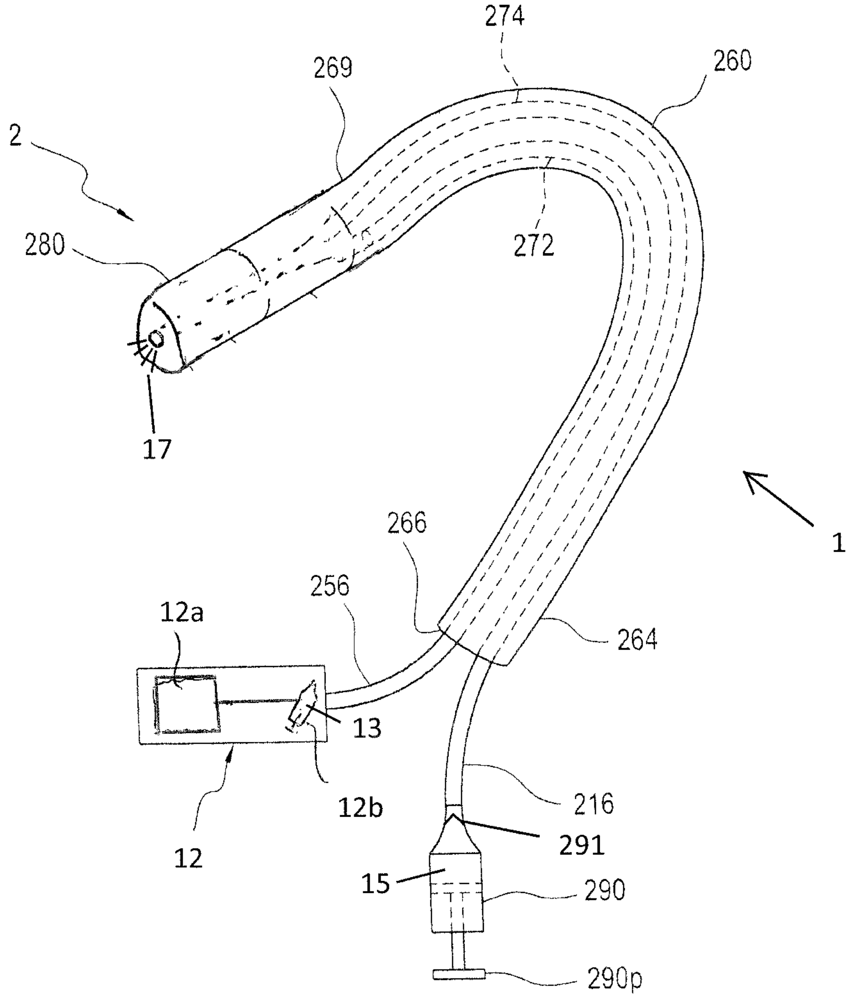
FIG. 4 is a perspective view of the delivery apparatus with the delivery catheter and a syringe containing an iodinated contrast medium.

With reference to FIG. 4, the delivery apparatus 1 is shown. The delivery catheter 2 includes a dual lumen catheter 260 connecting a Venturi-agitating tip assembly 280 to pressurized medical carbon dioxide ($CO_2$) 13 from the pressure delivery syringe 12*b* of the compressed medical fluid unit 12 and an iodinated contrast medium 15 from a contrast syringe 290. The contrast syringe 290 includes a one-way valve 291 at its outlet to ensure that iodinated contrast medium 15 from the contrast syringe 290 only flows out of the contrast syringe 290. The delivery catheter 2 includes a first end (or distal end) 262 having the Venturi-agitating tip assembly 280 and a second end (or proximal end) 264 to which the pressure delivery syringe 12*b* of the compressed medical fluid unit 12 and the contrast syringe 290 are fluidly connected for the passage of pressurized medical carbon dioxide ($CO_2$) 13 and iodinated contrast medium 15. As will be appreciated based upon the following disclosure, the dual lumen catheter 260 is connected to the Venturi-agitating tip assembly 280 by securing a first lumen 272 and a second lumen 274 of the dual lumen catheter 260 to the Venturi-agitating tip assembly 280. The provision of the Venturi-agitating tip assembly 280 at the distal end of the delivery catheter 2 allows for the mixing of pressurized medical carbon dioxide ($CO_2$) 13 and the iodinated contrast medium 15 immediately adjacent the discharge point.

A micro-hose 256 connects the pressure delivery syringe 12*b* of the compressed medical fluid unit 12 to the first lumen 272 of the dual lumen catheter 260 at a proximal first end 266 of the dual lumen catheter 260 for the transmission of the pressurized medical carbon dioxide ($CO_2$) 13 from the pressure delivery syringe 12*b* of the compressed medical fluid unit 12 to the Venturi-agitating tip assembly 280. As such, pressurized medical carbon dioxide ($CO_2$) 13 leaving the pressure delivery syringe 12*b* of the compressed medical fluid unit 12 enters the first lumen 272 of the dual lumen catheter 260 via the micro-hose 256. After passing through the first lumen 272 of the dual lumen catheter 260, the pressurized medical carbon dioxide ($CO_2$) 13 passes through the inlet of the Venturi-agitating tip assembly 280 and enters the Venturi-agitating tip assembly 280 of the delivery catheter 2. As will be explained below in greater detail, the medical contrast suspension of carbon dioxide ($CO_2$) and iodinated contrast medium 17 generated at the Venturi-agitating tip assembly 280 is applied as required.

As to the connection of the iodinated contrast medium 15 to the delivery catheter 2, the iodinated contrast medium 15 is delivered to the second lumen 274 of the dual lumen catheter 260 at the proximal first end 266 thereof, and ultimately to the Venturi-agitating tip assembly 280, via a container, in particular, the contrast syringe 290, connected to the second lumen 274 of the dual lumen catheter 260 by a supply line 216. As discussed above, the contrast syringe 290 includes a one-way valve 291 at its outlet to ensure that iodinated contrast medium 15 from the contrast syringe 290 only flows out of the contrast syringe 290. After passing through the second lumen 274 of the dual lumen catheter 260, the iodinated contrast medium 15 from the contrast syringe 290 travels into the Venturi-agitating tip assembly 280 where it is combined with pressurized medical carbon dioxide ($CO_2$) 13 from the pressure delivery syringe 12*b* of the compressed medical fluid unit 12 to form an enriched medical contrast suspension 17.

Figure 5A:
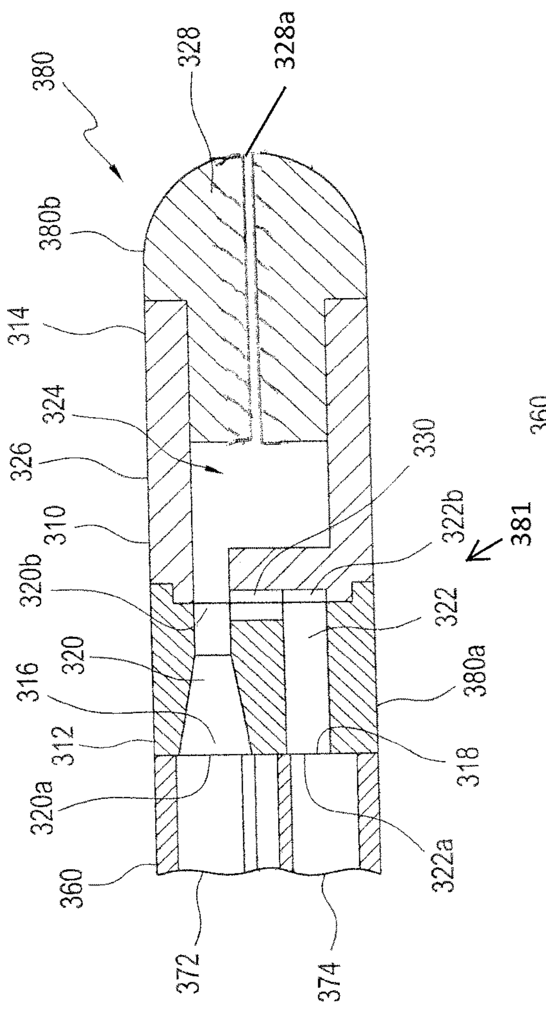
FIGS. 5A, 5B and 5C respectively show a longitudinal cross sectional view, a perspective view, and a perspective cross sectional view of a Venturi-agitating tip assembly in accordance with a first embodiment.
Figure 5C:
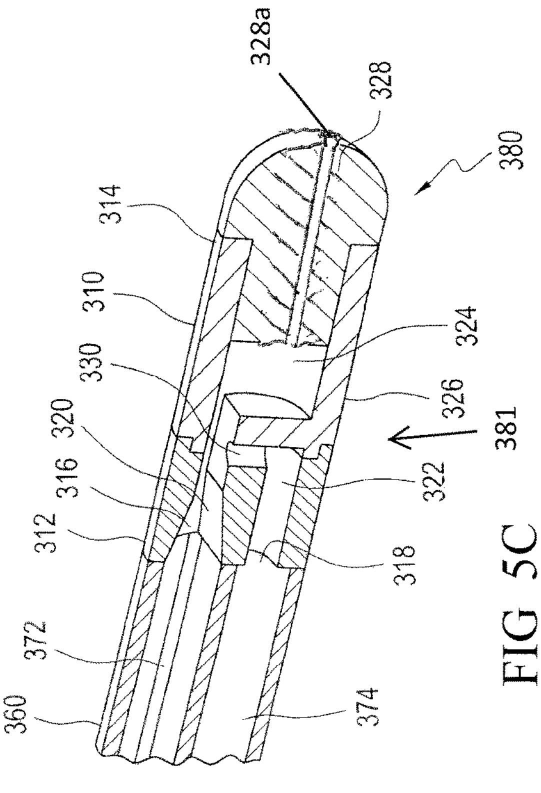
Figure 5B:
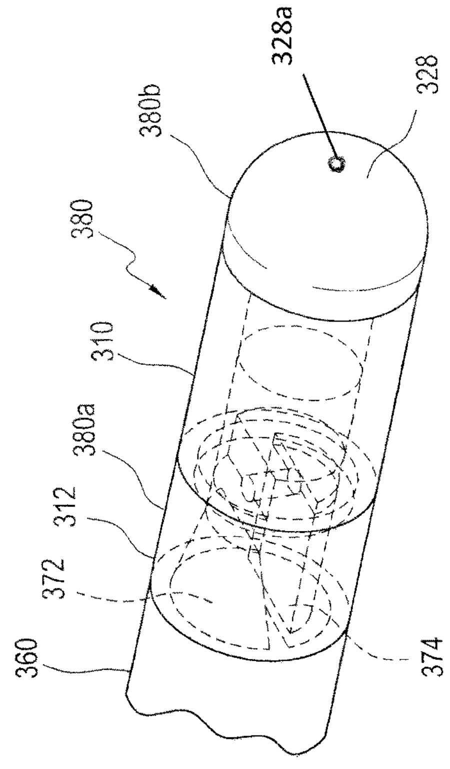

It is appreciated various tip assemblies and enriched medical contrast suspension generating structures may be employed in accordance with the present invention. In accordance with a first embodiment as shown with reference to FIGS. 5A-5C, the Venturi-agitating tip assembly 380 employs a Venturi arrangement with a mixing chamber 324. The Venturi-agitating tip assembly 380 has a proximal first end 380*a* and a distal second end 380*b*. The Venturi-agitating tip assembly 380 includes a hollow cylindrical elongated body 310 having a proximal first end 312, which coincides with the proximal first end 380*a* of the Venturi-agitating tip assembly 380, and a distal second end 314. The proximal first end 380*a* of the Venturi-agitating tip assembly 380 includes a multi-channel arrangement 381 including first and second inputs 316, 318 for attachment to the dual lumen catheter 360. The first and second inputs 316, 318 respectively lead to a first channel 320 and a second channel 322 of the multi-channel arrangement 381 of the Venturi-agitating tip assembly 380. The first and second channels 320, 322 lead to, and are in fluid communication with, the mixing chamber 324 (which also forms part of the multi-channel arrangement 381) located in the central portion 326 of the Venturi-agitating tip assembly 380, that is, between the proximal first end 380*a* and the distal second end 380*b*. Located at the distal second end 380*b* of the Venturi-agitating tip assembly 380, and secured to the distal second end 314 of the elongated body 310, is a spray tip 328 directing the enriched medical contrast suspension in a spray pattern onto the inner lumen of a vessel.

The first channel 320 and the second channel 322 are interconnected in a manner creating a Venturi effect causing the pressurized medical carbon dioxide ($CO_2$) to effectively pull the iodinated contrast medium through the second channel 322 and into the mixing chamber 324. This is achieved by providing with the first channel 320 with a reduced diameter as it extends from the proximal first end 312 of the elongated body 310 (that is, the first end 320*a* of the first channel 320) to the central portion 326 of the Venturi-agitating tip assembly 380 (that is, the second end 320*b* of the first channel 320). In accordance with a preferred embodiment, the diameter of the first channel 320 decreases from a diameter of 0.038 inches adjacent the proximal first end 312 of the elongated body 310 to a diameter of 0.017 inches adjacent the mixing chamber 324.

As mentioned above, the second channel 322 is in fluid communication with the first channel 320. This is achieved by the provisional of a transverse channel 330 connecting the second end 320*b* of the first channel 320 with the second end 322*b* of the second channel 322. In particular, the second channel 322 includes a first end 322*a* adjacent the proximal first end 312 of the elongated body 310 and a second end 322*b* adjacent the mixing chamber 324 (although not directly in fluid communication with the mixing chamber 324) and the transverse channel 330. In accordance with a preferred embodiment, the diameter of the second channel 322 is 0.031 inches and remains consistent as it extends from the first end 322*a* thereof to the second end 322*b* thereof.

The first lumen 372 of the dual lumen catheter 360 supplies the pressurized medical carbon dioxide ($CO_2$) and the second lumen 374 supplies the iodinated contrast medium. As such, the first lumen 372 is connected to, and in fluid communication with, the first channel 320 of the Venturi-agitating tip assembly 380 and the second lumen 374 is connected to, and in fluid communication with, the second channel 322 of the Venturi-agitating tip assembly 380. In practice, the iodinated contrast medium from the contrast syringe 290 travels through the second lumen 374 of the dual lumen catheter 360 and into the second channel 322 when pressurized medical carbon dioxide ($CO_2$) gas enters the first channel 320 and passes the transverse channel 330 as it flows into the mixing chamber 324 after being actuated and released from the pressure delivery syringe 12*b* of the compressed medical fluid unit 12. The pressurized medical carbon dioxide ($CO_2$) entering, and passing through, the Venturi-agitating tip assembly 380 imparts negative pressure on the iodinated contrast medium in the contrast syringe 290 and draws the iodinated contrast medium from the contrast syringe 290 through the second channel 322, through the second lumen 374 of the dual lumen catheter 360, through the transverse channel 330, and into the mixing chamber 324 due to the Venturi effect. The iodinated contrast medium and the pressurized medical carbon dioxide ($CO_2$) are then mixed within the mixing chamber 324 to form an enriched medical contrast suspension. The syringe plunger 290*p* is used to regulate or stop flow of iodinated contrast medium from the contrast syringe 290.

The pressurized medical carbon dioxide ($CO_2$) and iodinated contrast medium mixing in the mixing chamber 324 are then forced through the spray tip 328 from which the enriched medical contrast suspension is sprayed upon the inner lumen of a vessel. The spray tip 328 includes an outlet 328*a* through which the enriched medical contrast suspension passes. The force of the pressurized medical carbon dioxide ($CO_2$) traveling through the Venturi-agitating tip assembly 380 and exiting through the spray tip as part of an enriched medical contrast suspension projects the enriched medical contrast suspension from the distal second end 384 of the Venturi-agitating tip assembly 380 as a spray and onto the inner lumen of a vessel.

In accordance with a second embodiment as shown with reference to FIGS. 6A-6D, a Venturi-agitating tip assembly 480 employs a sintered material tip 428 in conjunction with a multi-channel arrangement 481 where the pressurized medical carbon dioxide ($CO_2$) and iodinated contrast medium are mixed and forced through the spray tip 428. The Venturi-agitating tip assembly 480 includes a proximal first end 480*a* and a distal second end 480*b*. The Venturi-agitating tip assembly 480 includes a hollow cylindrical elongated body 410 having a proximal first end 412, which coincides with the proximal first end 480*a* of the Venturi-agitating tip assembly 480, and a distal second end 414. The Venturi-agitating tip assembly 480 is adapted for use with a dual lumen catheter 460, in particular a dual lumen catheter having concentric lumens, wherein the outer first lumen 472 is annular shaped for the passage of pressurized medical carbon dioxide ($CO_2$) (and has an outer diameter of 0.092 inches at the outer wall thereof and an inner diameter of 0.042 inches at the inner wall thereof) and the inner second lumen 474 is circular shaped for the passage of the iodinated contrast medium (and has a diameter of 0.030 inches). The inner second lumen 474 is supported within the outer first lumen 472 by first and second radially extending rib members 473*a*, 473*b* (each having a thickness of 0.006 inches) that extend from the outer surface of the second lumen 474 to the inner surface of the outer first lumen 472. In this way the outer first lumen 472 is divided into first and second semicircular passageways 475*a*, 475*b*.

Figure 6D:
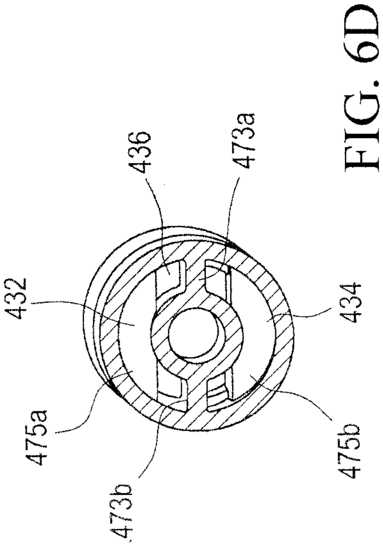
FIGS. 6A, 6B, 6C and 6D respectively show perspective view, a longitudinal cross-sectional perspective view, an exploded view, and a lateral cross-sectional view of a Venturi-agitating tip assembly in accordance with a second embodiment.
Figure 6C:
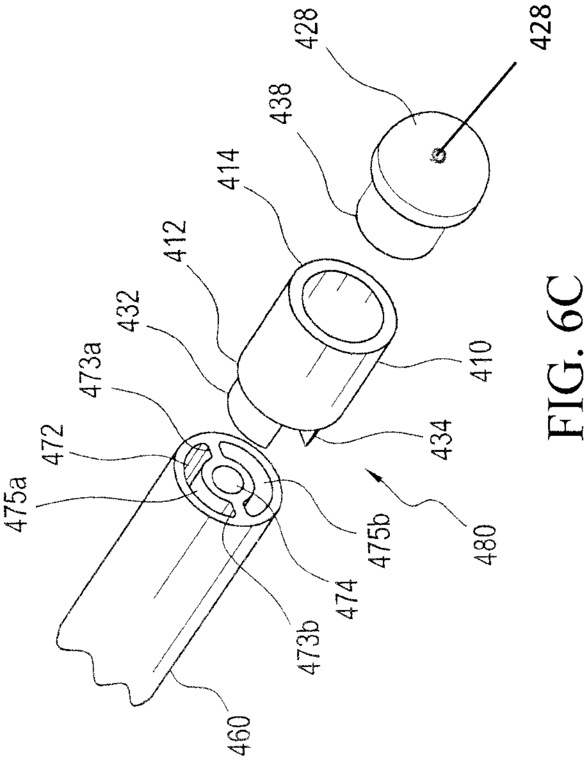
Figure 6A:
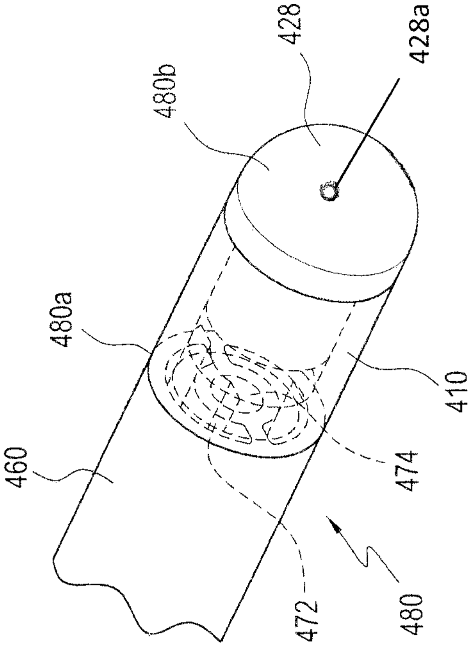
Figure 6B:
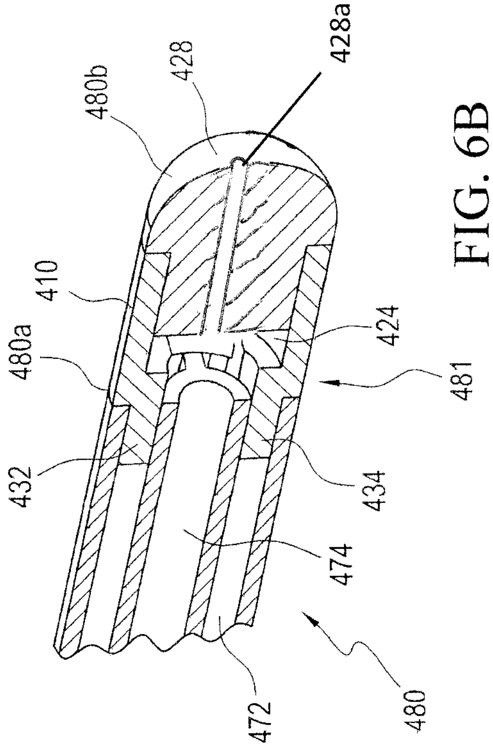

The proximal first end 480*a* of the Venturi-agitating tip assembly 480, in particular, the proximal first end 412 of the elongated body 410 is formed with two projections 432, 434 shaped and dimensioned for engagement within the outer first lumen 472 of the catheter 460 in a manner blocking a substantial portion of the outer first lumen 472. The two projections 432, 434 are arcuate members shaped and dimensioned to respectively block substantial portions of the first and second semicircular passageways 475*a*, 475*b* while creating four small passageways 436, each of approximately 0.031 inches (along the Y-axis as shown in FIG. 6D) by 0.050 inches (along the X-axis as shown in FIG. 6D) for the passage of pressurized medical carbon dioxide ($CO_2$) therethrough. The four small passageways 436 are defined by spaces existing between the edges of the arcuate members 432, 434 and the first and second radially extending rib members 473*a*, 473*b*.

The remainder of the Venturi-agitating tip assembly 480 includes a central mixing chamber 424 that is in fluid communication with the second lumen 474 and the four small passageways 436 feeding pressurized medical carbon dioxide ($CO_2$) from the first lumen 472. Secured to, and closing off, the second end 414 of the elongated body 410 is a spray tip 428, which is positioned at the distal second end 480*b* of the Venturi-agitating tip assembly 480. Attachment of the spray tip 428 to the elongated body 410 is achieved by providing the spray tip 428 with a projection 438 that seats within the opening at the second end 414 of the elongated body 410.

The first lumen 472 and the second lumen 474 are interconnected in a manner causing the pressurized medical carbon dioxide ($CO_2$) to effectively pull the iodinated contrast medium through the second lumen 474 and into the mixing chamber 424. In practice, the iodinated contrast medium from the contrast syringe 290 travels through the second lumen 474 of the dual lumen catheter 460 and into the mixing chamber 424 when pressurized medical carbon dioxide ($CO_2$) passes through the four small passageways 436 and enters the mixing chamber 424 (where the iodinated contrast medium from the contrast syringe 290 and the pressurized medical carbon dioxide ($CO_2$) mix to form an enriched medical contrast suspension) after being actuated and released from the pressure delivery syringe 12*b* of the compressed medical fluid unit 12. The pressurized medical carbon dioxide ($CO_2$) entering, and passing through, the mixing chamber 424 imparts negative pressure on the iodinated contrast medium in the contrast syringe 290 and draws the iodinated contrast medium from the contrast syringe 290 through the second lumen 474 and into the mixing chamber 424. The syringe plunger 290*p* is used to regulate or stop flow of iodinated contrast medium from the contrast syringe 290.

The pressurized medical carbon dioxide ($CO_2$) and iodinated contrast medium mixing in the mixing chamber 424 are then forced through the spray tip 428 from which an enriched medical contrast suspension is sprayed upon the inner surface of a lumen. The spray tip 428 includes an outlet 428*a* through which the enriched medical contrast suspension passes. The force of the pressurized medical carbon dioxide ($CO_2$) traveling through the Venturi-agitating tip assembly 480 and exiting through the spray tip 428 as part of an enriched medical contrast suspension projects the enriched medical contrast suspension from the distal second end 484 of the Venturi-agitating tip assembly 480 as a spray and onto the inner lumen of a vessel.

Figure 7B:
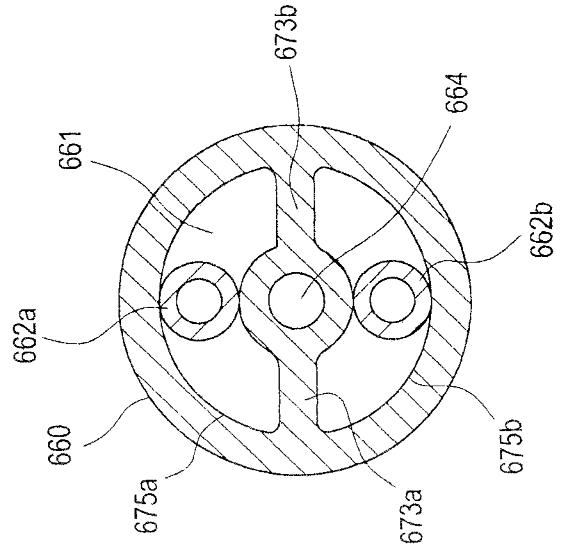
FIGS. 7A and 7B respectively show longitudinal cross-sectional view and a lateral cross-sectional view of a Venturi-agitating tip assembly in accordance with a third embodiment.
Figure 7A:
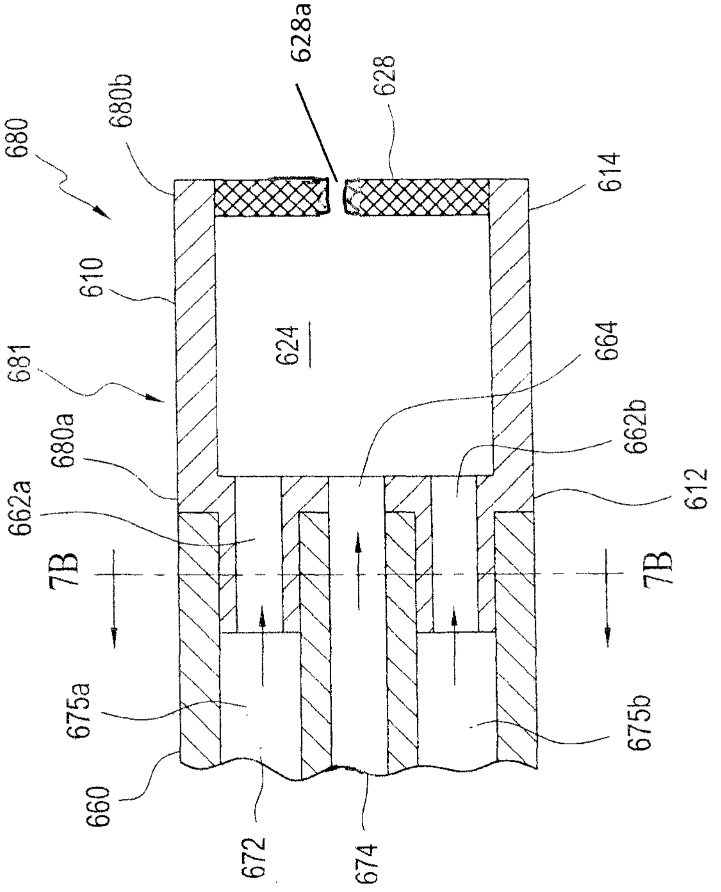
Figure 8A:
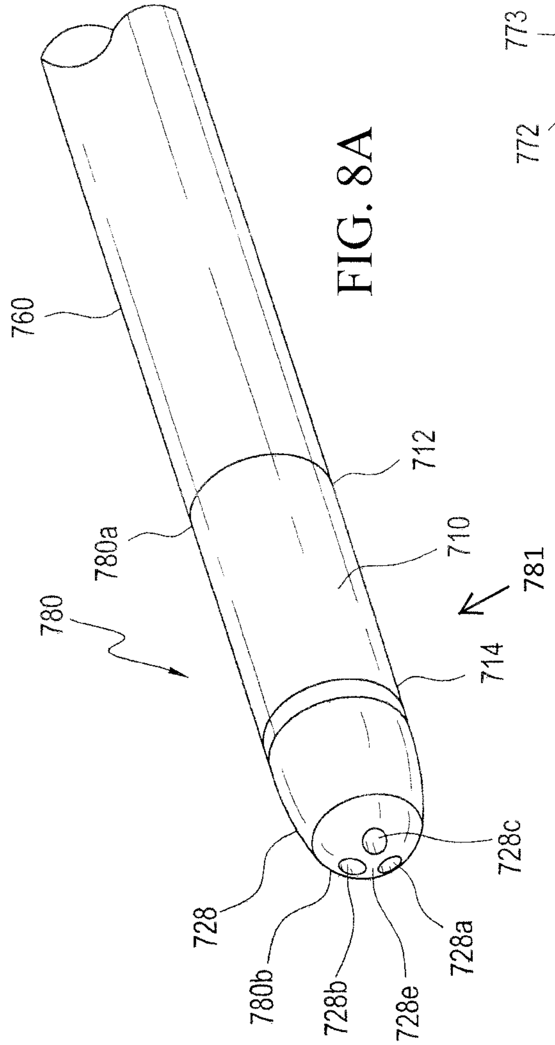
FIGS. 8A, 8B, 8C, 8D and 8E respectively show a perspective view, an exploded view, a front partial cross-sectional view, a rear partial cross-sectional view, and a lateral cross-sectional view in accordance with a fourth embodiment.
Figure 8B:
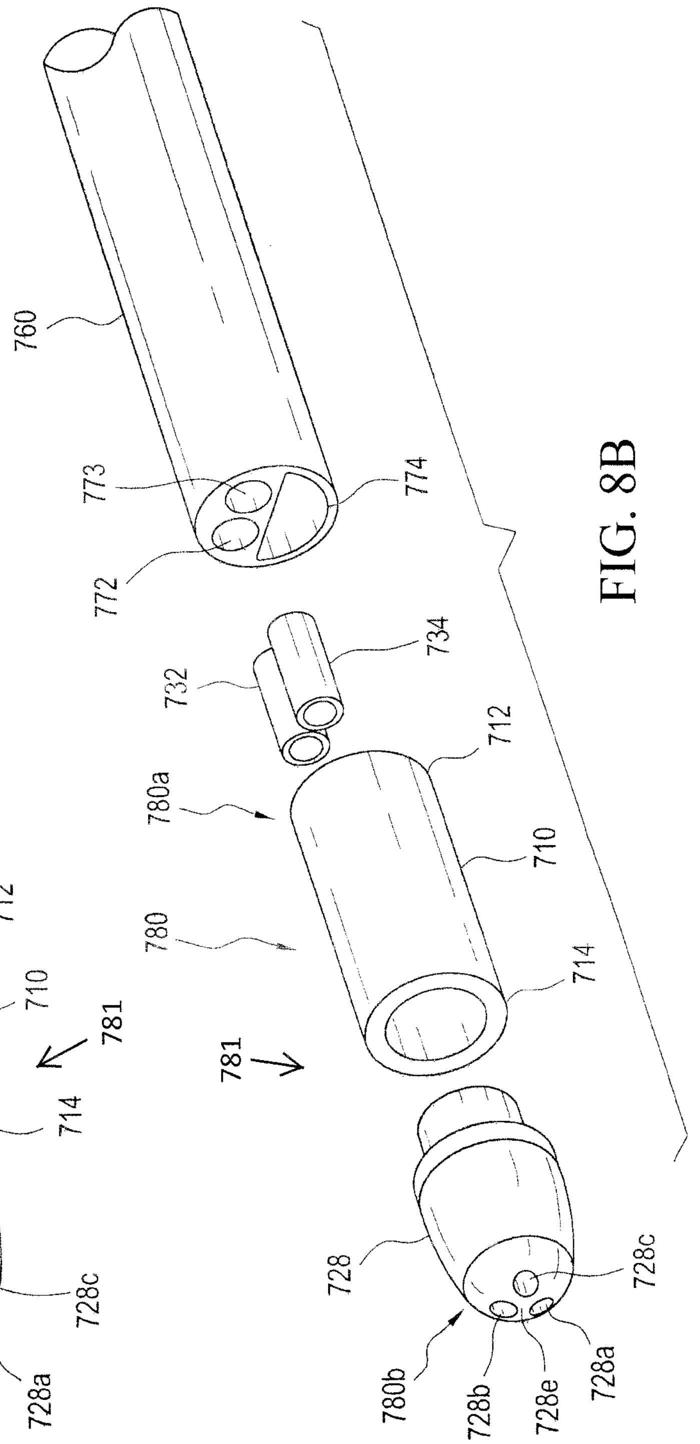
Figure 8C:
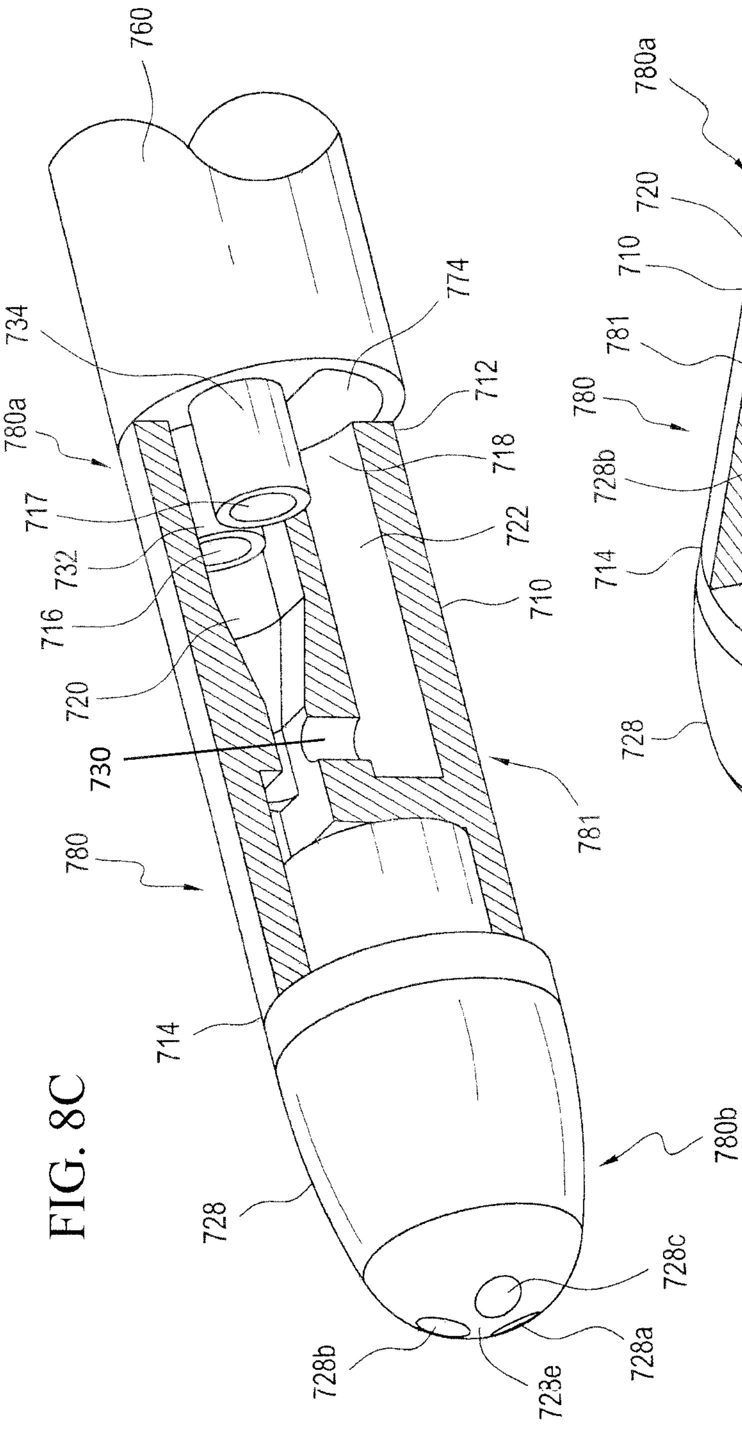
Figure 8D:
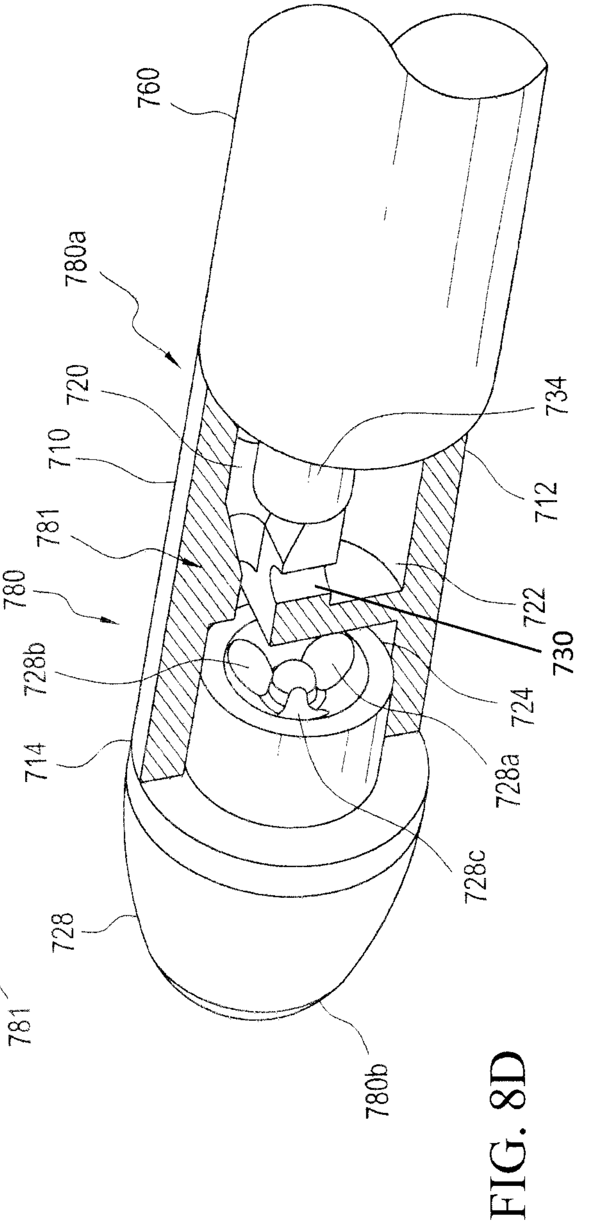
Figure 8E:
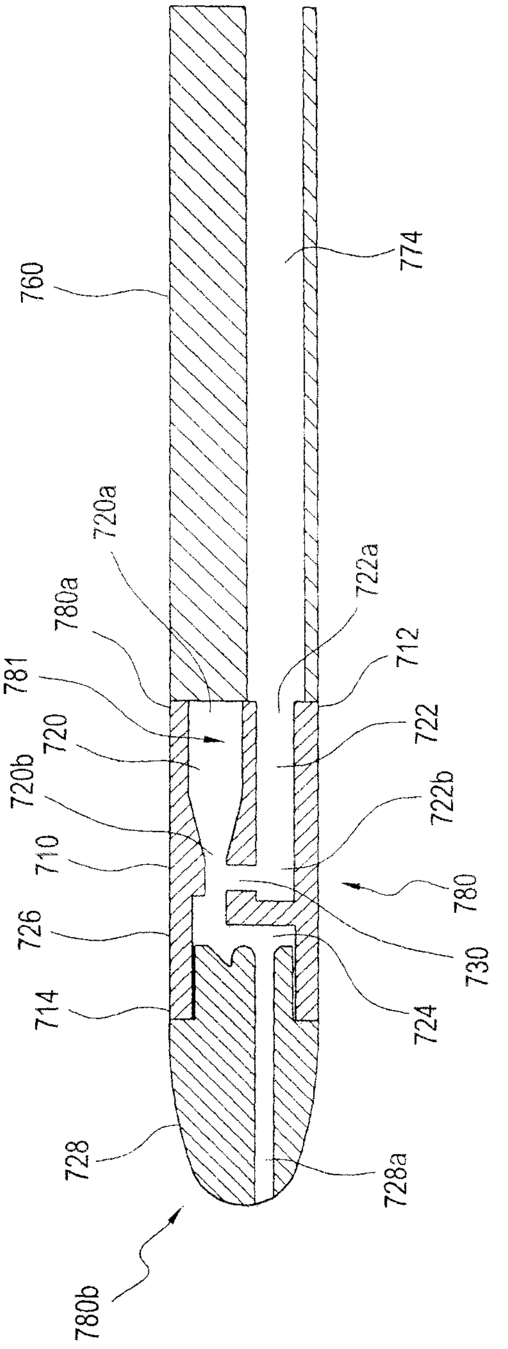

In accordance with a third embodiment as shown with reference to FIGS. 7A and 7B, a Venturi-agitating tip assembly 680 employs a spray tip 628 in conjunction with a multi-channel arrangement 681 where the pressurized medical carbon dioxide ($CO_2$) and iodinated contrast medium are mixed in the Venturi-agitating tip assembly 680 and forced through the spray tip 628. The Venturi-agitating tip assembly 680 includes a proximal first end 680*a* and a distal second end 680*b*. The Venturi-agitating tip assembly 680 includes a cylindrical hollow elongated body 610 having a proximal first end 612, which coincides with the proximal first end 680*a* of the Venturi-agitating tip assembly 680, and a distal second end 614, which coincides with the distal second end 680*b* of the Venturi-agitating tip assembly 680. The Venturi-agitating tip assembly 680 is adapted for use with a dual lumen catheter 660, in particular a dual lumen catheter having concentric lumens, wherein the outer first lumen 672 is annular shaped for the passage of pressurized medical carbon dioxide ($CO_2$) (and has an outer diameter of 0.092 inches at the outer wall thereof and an inner diameter of 0.042 inches at the inner wall thereof) and the inner second lumen 674 is circular shaped for the passage of the iodinated contrast medium (and has a diameter of 0.030 inches). The inner second lumen 674 is supported within the outer first lumen 672 by first and second radially extending rib members 673*a*, 673*b* (as shown in FIG. 7B) that extend from the outer surface of the second lumen 674 to the inner surface of the outer first lumen 672. In this way the outer first lumen 672 is divided into first and second semicircular passageways 675*a*, 675*b*.

The proximal first end 612 of the elongated body 610 at the proximal first end 680*a* of the Venturi-agitating tip assembly 680 includes an end wall 661 (created by adhesive injected to limit flow from the first lumen 672) with two projecting channels 662*a*, 662*b* (each with a diameter of 0.015 inches) shaped and dimensioned for engagement with the first and second semicircular passageways 675*a*, 675*b*.

The end wall 660 of the proximal first end 612 of the elongated body 610 is also provided with a central aperture 664 shaped and dimensioned for alignment with the second lumen 674. The remainder of the proximal first end 612 of the elongated body 610 is closed off thus limiting and controlling the flow of materials into the central mixing chamber 624.

The remainder of the Venturi-agitating tip assembly 680 includes a central mixing chamber 624 that is in fluid communication with the second lumen 674 and the two projecting channels 662*a*, 662*b* feeding pressurized medical carbon dioxide ($CO_2$) from the first lumen 672. As a result, and as will be explained below in greater detail, the iodinated contrast medium and the pressurized medical carbon dioxide ($CO_2$) are mix within the mixing chamber 624 to form an enriched medical contrast suspension. Secured to, and closing off, the second end 614 of the elongated body 610 is a spray tip 628, which is positioned at the distal second end 680*b* of the Venturi-agitating tip assembly 680.

The first lumen 672 and the second lumen 674 are interconnected in a manner causing the pressurized medical carbon dioxide ($CO_2$) to effectively pull the iodinated contrast medium through the second lumen 674 and into the mixing chamber 624. In practice, the iodinated contrast medium from the contrast syringe 290 travels through the second lumen 674 of the dual lumen catheter 660 and into the mixing chamber 624 when pressurized medical carbon dioxide ($CO_2$) passes through the first and second projecting channels 662*a*, 662*b* and enters the mixing chamber 624 after being actuated and released from the pressure delivery syringe 12*b* of the compressed medical fluid unit 12. The pressurized medical carbon dioxide ($CO_2$) entering, and passing through, the mixing chamber 624 imparts negative pressure on the iodinated contrast medium in the contrast syringe 290 and draws the iodinated contrast medium from the contrast syringe 290 through second lumen 674 and into the mixing chamber 624. The syringe plunger 290*p* is used to regulate or stop flow of iodinated contrast medium from the contrast syringe 290.

The pressurized medical carbon dioxide ($CO_2$) and iodinated contrast medium mixing in the mixing chamber 624 are then forced through the spray tip 628 from which an enriched medical contrast suspension is sprayed. The spray tip 628 includes an outlet 628*a* through which the enriched medical contrast suspension passes. The force of the pressurized medical carbon dioxide ($CO_2$) traveling through the Venturi-agitating tip assembly 680 and exiting through the spray tip as part of an enriched medical contrast suspension projects the enriched medical contrast suspension from the distal second end 684 of the Venturi-agitating tip assembly 680 as a spray and onto the inner lumen of a vessel.

In accordance with a fourth embodiment as shown with reference to FIGS. 8A-8E, a Venturi-agitating tip assembly 780 employs a spray tip 728 in conjunction with a multi-channel arrangement 781 where the pressurized medical carbon dioxide ($CO_2$) and iodinated contrast medium are mixed to form an enriched medical contrast suspension and forced through the spray tip 728. The Venturi-agitating tip assembly 780 includes proximal first end 780*a* and a distal second end 780*b*. The Venturi-agitating tip assembly 780 includes a hollow cylindrical elongated body 710 having a proximal first end 712, which coincides with the proximal first end 780*a* of the Venturi-agitating tip assembly 780, and a distal second end 714. The Venturi-agitating tip assembly 780 is adapted for use with a multi-lumen catheter 760, in particular a triple lumen catheter having parallel lumens, wherein the first and second lumens 772, 773 are circular shaped (each with a diameter of 0.039 inches) and are dimensioned for the passage of pressurized medical carbon dioxide ($CO_2$) and the third lumen 774 is semi-circular shaped (with a radius of 0.047 inches) and is dimensioned for the passage of the iodinated contrast medium.

The proximal first end 712 of the elongated body 710 at the proximal first end 780*a* of the Venturi-agitating tip assembly 780 includes first, second and third inputs 716, 717, 718 for attachment to the multi-lumen catheter 760. The first and second inputs 716, 717 lead to a first channel 720 and the third input 718 to a second channel 722. As such, the proximal first end 712 of the elongated body 710 at the proximal first end 780*a* of the Venturi-agitating tip assembly 780 is formed with two circular tubular projections 732, 734, defining the first and second inputs 716, 717. The circular tubular projections 732, 734 (each with an inner diameter of 0.027 inches and an outer diameter of 0.039 inches) are shaped and dimensioned for engagement within the first and second lumens 772, 773 of the catheter 760 in a manner allowing for the flow of fluid from the first and second lumens 772, 773 and into the Venturi-agitating tip assembly 780. The two circular tubular projections 732, 734 are shaped and dimensioned to fit within the first and second lumens 772, 773 while maintaining passageways for the passage of pressurized medical carbon dioxide ($CO_2$) therethrough.

The first and second channels 720, 722 lead to, and are in fluid communication with, a mixing chamber 724 located in the central portion 726 of the Venturi-agitating tip assembly 780, that is, between the proximal first end 712 and the distal second end 714 of the elongated body. Secured to the distal second end 714 of the elongated body 710, and positioned at the distal second end 780*b* of the Venturi-agitating tip assembly, is a spray tip 728 having three passageways 728*a*, 728*b*, 728*c* extending from the mixing chamber 724 to the exterior at the distal end of the Venturi-agitating tip assembly 780.

The first channel 720 and the second channel 722 are interconnected in a manner creating a Venturi effect causing the pressurized medical carbon dioxide ($CO_2$) to effectively pull the iodinated contrast medium through the second channel 722 and into the mixing chamber 724. This is achieved by providing the first channel 720 with a reduced diameter (decreasing from 0.038 inches to 0.017 inches) as it extends from the proximal first end 712 of the elongated body 710 (that is, the first end 720*a* of the first channel 720) to the central portion 726 of the Venturi-agitating tip assembly 780 (that is, the second end 720*b* of the first channel 720). In accordance with a preferred embodiment, the diameter of the first channel 720 decreases from a diameter of 0.038 inches adjacent the proximal first end 712 of the elongated body 710 to a diameter of 0.017 inches adjacent the mixing chamber 724.

As mentioned above, the second channel 722 is in fluid communication with the first channel 720. This is achieved by the provisional of a transverse channel 730 connecting the second end 720*b* of the first channel 720 with the second end 722*b* of the second channel 722. In particular, the second channel 722 includes a first end 722*a* adjacent the proximal first end 712 of the elongated body 710 and a second end 722*b* adjacent the mixing chamber 724 (although not directly in fluid communication with the mixing chamber 724) and the transverse channel 730. In accordance with a preferred embodiment, the diameter of the second channel 722 is 0.047 inches and remains consistent as it extends from the first end 722*a* thereof to the second end 722*b* thereof.

The first and second lumens 772, 773 supply the pressurized medical carbon dioxide ($CO_2$) and the third lumen 774 supplies the iodinated contrast medium. As such, the first and second lumens 772, 773 are connected to, and in fluid communication, with the first channel 720 of the Venturi-agitating tip assembly 780 and the third lumen 774 is connected to, and in fluid communication, with the second channel 722 of the Venturi-agitating tip assembly 780. In practice, the iodinated contrast medium from contrast syringe 290 travels through third lumen 774 of multi-lumen lumen catheter 760 and into the second channel 722 when pressurized medical carbon dioxide ($CO_2$) gas enters the first channel 720 and passes the transverse channel 730 (having a size of 0.020 inches) into the mixing chamber 724 after being actuated and released from the pressure delivery syringe 12*b* of the compressed medical fluid unit 12. The pressurized medical carbon dioxide ($CO_2$) entering, and passing through, the Venturi-agitating tip assembly 780 imparts negative pressure on the iodinated contrast medium in contrast syringe 290 and draws the iodinated contrast medium from the contrast syringe 290 through second channel 722, through the third lumen 774 of the dual lumen catheter 760, and into the mixing chamber 724 due to the Venturi effect. The syringe plunger 290*p* is used to regulate or stop flow of iodinated contrast medium from the contrast syringe 290.

The pressurized medical carbon dioxide ($CO_2$) and iodinated contrast medium mixing in the mixing chamber 724 form an enriched medical contrast suspension that is then forced through the passageways 728*a* -c of the spray tip 728. The force of the pressurized medical carbon dioxide ($CO_2$) traveling through the Venturi-agitating tip assembly 780 and exiting through the spray tip 728 as part of an enriched medical contrast suspension projects the enriched medical contrast suspension from the distal second end 784 of the Venturi-agitating tip assembly 780 as a spray and onto the inner lumen of a vessel.

In accordance with yet another embodiment, the concepts underlying the present invention may be applied in the provision of a medical suspension delivery needle. Such a medical suspension delivery needle would be useful in accessing vessel locations that are inaccessible by the catheter described above. The needle embodiment may also be useful in accessing locations that are limited in length and might not require the use of the delivery catheter described above.

While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

While the preferred embodiments have been shown and described, it will be understood that there is no intent to limit the invention by such disclosure, but rather, it is intended to cover all modifications and alternative constructions falling within the spirit and scope of the invention.

The invention claimed is:

1. A medical contrast suspension generating delivery apparatus, comprising:

a Venturi-agitating tip assembly;

a source of pressurized medical carbon dioxide;

a source of an iodinated contrast medium;

a dual lumen catheter connecting the Venturi-agitating tip assembly to the source of pressurized medical carbon dioxide and the source of the iodinated contrast medium.

2. The delivery apparatus according to claim 1, wherein the source of pressurized medical carbon dioxide includes a pressure delivery syringe of a compressed medical fluid unit.

3. The delivery apparatus according to claim 2, wherein the source of the iodinated contrast medium includes a contrast syringe.

4. The delivery apparatus according to claim 3, wherein a micro-hose connects the source of pressurized medical carbon dioxide to a first lumen of the dual lumen catheter.

5. The delivery apparatus according to claim 4, wherein the source of the iodinated contrast medium is connected to a second lumen of the dual lumen catheter to deliver the iodinated contrast medium to the second lumen of the dual lumen catheter.

6. The delivery apparatus according to claim 3, wherein the contrast syringe includes a one-way valve at its outlet to ensure that the iodinated contrast medium from the contrast syringe only flows out of the contrast syringe.

7. The delivery apparatus according to claim 1, wherein the source of the iodinated contrast medium includes a contrast syringe.

8. The delivery apparatus according to claim 7, wherein the contrast syringe includes a one-way valve at its outlet to ensure that the iodinated contrast medium from the contrast syringe only flows out of the contrast syringe.

9. The delivery apparatus according to claim 1, wherein a micro-hose connects the source of pressurized medical carbon dioxide to a first lumen of the dual lumen catheter.

10. The delivery apparatus according to claim 9, wherein the source of the iodinated contrast medium is connected to a second lumen of the dual lumen catheter to deliver the iodinated contrast medium to the second lumen of the dual lumen catheter.

* * * * *